(12) United States Patent
Singh et al.

(10) Patent No.: US 11,911,263 B2
(45) Date of Patent: Feb. 27, 2024

(54) PACKAGING-ASSISTED ACTUATION FOR AN INTRAOCULAR LENS CARTRIDGE

(71) Applicant: Alcon Inc., Fribourg (CH)

(72) Inventors: Sudarshan B. Singh, Euless, TX (US); Todd Taber, Keller, TX (US); Yinghui Wu, Cedar Hill, TX (US); Douglas Brent Wensrich, Bedford, TX (US); Trevor Haney, Jenison, MI (US); Andrew Check, Kalamazoo, MI (US); Justin Benaquisto, New Baltimore, MI (US); Joe Marietta, Kalamazoo, MI (US); Jonathan Penrod, Kalamazoo, MI (US); Tim LaRoy, Kalamazoo, MI (US); Bryce Porter, Kalamazoo, MI (US)

(73) Assignee: Alcon Inc., Fribourg (CH)

( * ) Notice: Subject to any disclaimer, the term of this patent is extended or adjusted under 35 U.S.C. 154(b) by 731 days.

(21) Appl. No.: 16/999,480

(22) Filed: Aug. 21, 2020

(65) Prior Publication Data
US 2021/0052374 A1    Feb. 25, 2021

Related U.S. Application Data

(60) Provisional application No. 63/040,586, filed on Jun. 18, 2020, provisional application No. 62/890,859, filed on Aug. 23, 2019.

(51) Int. Cl.
*A61F 2/16* (2006.01)

(52) U.S. Cl.
CPC ............ *A61F 2/1691* (2013.01); *A61F 2/167* (2013.01); *A61F 2/1678* (2013.01); *A61F 2002/1683* (2013.01)

(58) Field of Classification Search
CPC ...... A61F 2/1691; A61F 1/167; A61F 2/1678; A61F 2/1672; A61F 2/1662; A61F 2/1675; A61F 2/16
See application file for complete search history.

(56) References Cited

U.S. PATENT DOCUMENTS

| 4,976,716 A | 12/1990 | Cumming |
| 8,403,941 B2 | 3/2013 | Peterson et al. |
| 8,647,382 B2 | 2/2014 | Kudo |
| 9,314,373 B2 | 4/2016 | Kudo |
| 9,421,092 B2 | 8/2016 | Brown |

(Continued)

FOREIGN PATENT DOCUMENTS

WO    2012027517 A2    3/2012

*Primary Examiner* — Tan-Uyen T Ho
*Assistant Examiner* — Bridget E. Rabaglia
(74) *Attorney, Agent, or Firm* — Patterson + Sheridan, LLP (57) ABSTRACT

Systems, methods, and apparatuses for storing and/or shipping an intraocular lens (IOL) cartridge are provided. A system comprises a packaging comprising a passage. The IOL cartridge is removably disposed within the passage. The IOL cartridge comprises a nozzle and a compartment configured to receive an IOL. The nozzle is in fluid communication with the compartment. The IOL cartridge further comprises a dial configured to rotate upon withdrawal of the IOL cartridge from the passage, wherein an inner surface of the dial is exposed to the compartment. The dial is configured to fold the IOL and release the IOL cartridge from the packaging upon rotation of the dial.

16 Claims, 8 Drawing Sheets

(56) References Cited

U.S. PATENT DOCUMENTS

| | | |
|---|---|---|
| 9,907,648 B2 | 3/2018 | Peterson et al. |
| 2008/0039862 A1 | 2/2008 | Tran |
| 2012/0158007 A1* | 6/2012 | Brown .................. A61F 2/1691 606/107 |
| 2014/0066946 A1 | 3/2014 | Aguilera et al. |
| 2020/0179101 A1 | 6/2020 | Flowers |
| 2020/0179103 A1 | 6/2020 | Auld |
| 2020/0188089 A1 | 6/2020 | Auld |
| 2020/0197170 A1 | 6/2020 | Auld |

\* cited by examiner

PACKAGING-ASSISTED ACTUATION FOR AN INTRAOCULAR LENS CARTRIDGE

TECHNICAL FIELD

The present disclosure generally relates to eye surgery and, more particularly, some embodiments may generally relate to systems, methods, and apparatuses for removably attaching a drive mechanism handpiece to an intraocular lens (IOL) cartridge that is actuated with assistance from packaging containing the IOL cartridge.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be preloaded in the insertion tool. In other instances, a separate bay may be loaded into the insertion tool. The plunger may engage the IOL to advance the IOL from the bay, through a nozzle, and into the eye.

SUMMARY

In an exemplary embodiment, the present disclosure provides a system for storing and/or shipping an intraocular lens (IOL) cartridge. The system comprises a packaging comprising a passage. The IOL cartridge is removably disposed within the passage. The IOL cartridge comprises a nozzle and a compartment configured to receive an IOL. The nozzle is in fluid communication with the compartment. The IOL cartridge further comprises a dial configured to rotate upon withdrawal of the IOL cartridge from the passage. The dial is configured to fold the IOL and release the IOL cartridge from the packaging upon rotation of the dial.

In another exemplary embodiment, the present disclosure provides a system for storing and/or shipping the IOL cartridge. The system comprises a packaging comprising a passage, wherein a ledge is disposed within the passage. The IOL cartridge is removably disposed within the passage. The IOL cartridge comprises a nozzle and a compartment configured to receive an IOL. The nozzle is in fluid communication with the compartment. The IOL cartridge further comprises a dial configured to rotate upon withdrawal of the IOL cartridge from the passage. The dial comprises a protrusion that is adjacent to the ledge. An inner surface of the dial is exposed to the compartment. The dial is configured to fold the IOL and release the IOL cartridge from the packaging upon rotation of the dial. The IOL cartridge further comprises a plunger case in fluid communication with the compartment, wherein a plunger is movably disposed within the plunger case.

In another exemplary embodiment, the present disclosure provides a method for delivery of an IOL into an eye. The method comprises inserting a handpiece into packaging comprising an IOL cartridge. The IOL cartridge comprises a nozzle and a compartment comprising the IOL. The nozzle is in fluid communication with the compartment. The IOL cartridge further comprises a dial, wherein an inner surface of the dial is exposed to the compartment. The IOL cartridge further comprises a plunger case in fluid communication with the compartment, wherein a plunger is movably disposed within the plunger case. The method further comprises rotating the handpiece to removably attach the handpiece to the IOL cartridge to form an insertion tool; and withdrawing the insertion tool from the packaging thereby rotating the dial to release the IOL cartridge from the packaging and to fold the IOL.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide an intraocular lens cartridge ("IOL cartridge") that is actuated with assistance from packaging. The IOL cartridge may initially be contained in the packaging for storage and/or shipping. The IOL cartridge includes a dial that is rotated, thereby releasing the IOL cartridge from the packaging, as the IOL cartridge is removed from the packaging. Rotation of the dial may also actuate a folding or splaying mechanism of the IOL cartridge. The IOL cartridge may be a preloaded cartridge that is preloaded with the IOL. The IOL cartridge may be part of a modular delivery system that includes a universal interface for removable attachment to various handpieces that include different types of drive mechanisms.

Particular embodiments of the present disclosure allow interchangeability between different handpieces such as disposable and reusable handpieces, and the IOL cartridge. The disposable handpieces may include manual drive mechanisms (e.g., manually actuated via pushing or screwing, and/or manually actuated via a fluid or a resilient member such as a spring) that are not electrically powered. The reusable handpieces may include the manual drive mechanisms as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure allow assembling of the handpiece to the IOL cartridge, delivering the IOL, and disengaging the handpiece from the used IOL cartridge, if needed. The universal interface allows the different types of handpieces to be easily paired to and utilized with the IOL cartridge for IOL implantation. After the IOL implantation, the IOL cartridge can be easily detached from the reusable handpiece.

The handpiece may be secured to the IOL cartridge by sliding an end of the handpiece into the packaging and over the plunger case of the IOL cartridge. Then the handpiece may be rotated to secure the handpiece to the IOL cartridge to form an insertion tool. In certain embodiments, the IOL cartridge may include a protrusion that mates with a slot of the handpiece to lock the handpiece to the IOL cartridge upon rotation of the handpiece. The insertion tool may then be removed (e.g., pulled) from the packaging. The pulling motion causes rotation of the dial that unlocks and releases the IOL cartridge from its initial locked position within the packaging. Additionally, as previously noted, the rotation of the dial may cause folding of the IOL or splaying of portions of the IOL within the IOL cartridge.

Once the insertion tool is formed and removed from the packaging, the IOL may be delivered into an eye. After the IOL delivery has been completed, the handpiece may be disconnected from the used IOL cartridge by rotating the handpiece in an opposite direction and pulling the handpiece away from the IOL cartridge.

Figure 1:
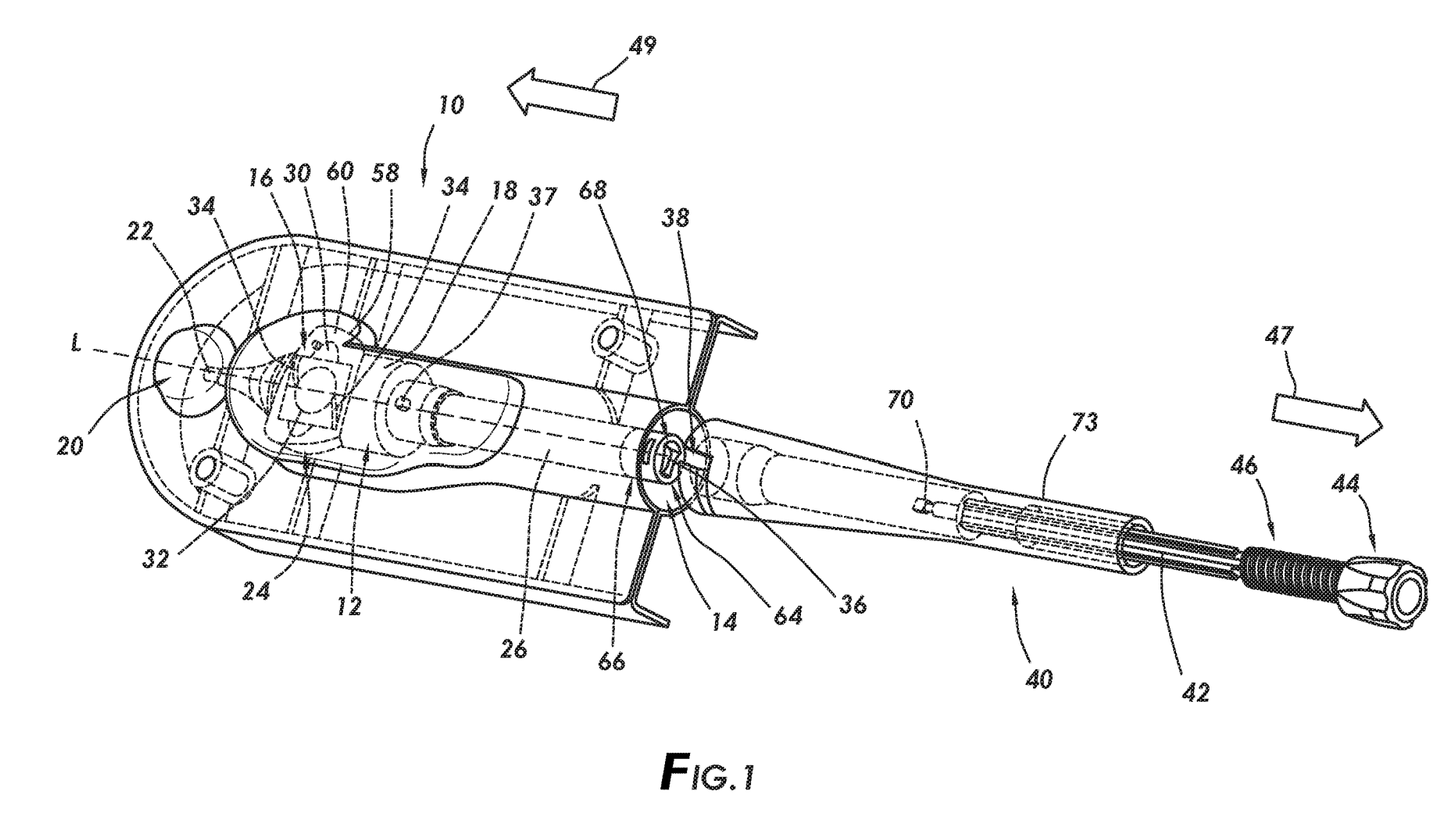
FIG. 1 illustrates a top perspective view of a packaging containing an IOL cartridge with a dial, in accordance with some embodiments of the present disclosure.

FIG. 1 illustrates a top perspective view of a packaging 10 used for storing and/or shipping an IOL cartridge 12 in accordance with some embodiments of the present disclosure. In this exemplary embodiment, the packaging 10 is illustrated as transparent to show the IOL cartridge 12 disposed within the packaging 10. The packaging 10 may be made of plastic and may include a passage 14 extending into a cavity 20. The cavity 20 may be at a distal end of the packaging 10 and may be in fluid communication with the passage 14. As shown, the passage 14 may be the only opening extending into the packaging 10 from the outside of the packaging 10 to allow extraction of the IOL cartridge 12.

The IOL cartridge 12 may include a housing 18 including a compartment 24 in fluid communication with a plunger case 26. The compartment 24 may be preloaded or contain an IOL 16 in some examples. The IOL cartridge 12 may also include a nozzle 22 extending from the housing 18. The nozzle 22 may be in fluid communication with the compartment 24. The nozzle 22 may be positioned in the cavity 20 while the IOL cartridge is positioned within the packaging 10. The cavity 20 may prevent damage to the nozzle 22 during shipping and/or storage of the IOL cartridge 12. The nozzle 22 provides a delivery channel for the IOL 16. The IOL cartridge 12 may also include a dial 30 which may be positioned within the passage 14 while the IOL cartridge 12 is disposed within the packaging 10. The dial 30 may be disposed above the compartment 24 and may be rotated to cause folding of the IOL 16 as the IOL cartridge 12 is extracted from the packaging 10.

The IOL 16 may include a lens portion 32 and haptic extensions 34. The haptic extensions 34 may be side struts (or other suitable extensions) extending from the lens portions 32 that may stabilize the IOL 16 when it may be disposed within the patient's eye. It should be understood that the IOL 16 is merely exemplary and that techniques disclosed herein may be used with any suitable IOL. For example, a modular IOL (not shown) that includes a lens portion disposable in a base with haptic extensions can also be used.

The IOL cartridge 12 may also include a projection 37 disposed on the housing 18 of the IOL cartridge 12 for insertion into a slot 38 of a handpiece 40. Upon rotation (e.g., 90°) of the handpiece 40, the projection 37 of the IOL cartridge 12 may be received and secured within the slot 38 of the handpiece 40. It should be noted that various handpieces may be used with different types of IOL cartridges. The handpiece 40 may include an electrically powered or a non-electrically powered drive mechanism that may include a push rod 42 extending along a length of the handpiece 40. The push rod 42 may be movably disposed within the handpiece 40 and may be manually actuated via a rotatable knob 44, which may cooperate with a fluid or a resilient member such as a spring 46 or another actuation mechanism. In general, for the purposes of discussing and describing the various components and features of the handpiece 40 and the IOL cartridge 12, reference to a proximal end or direction may refer to a direction more towards an end of the handpiece 40 comprising the rotatable knob 44, according to directional arrow 47. Likewise, reference to a distal end or direction may refer to a direction more towards an end of the IOL cartridge 12 comprising the nozzle 22, according to directional arrow 49.

In the illustrated embodiment, the dial 30 is in an initial non-rotated position to lock the IOL cartridge 12 in place within the packaging 10. The passage 14 includes a ledge 58 that aligns with a protrusion 60 of the dial 30 to contact and cause rotation of the dial 30 as the IOL cartridge 12 is pulled from the packaging 10 thereby releasing the IOL cartridge 12 from its initial locked position within the packaging 10. Rotation of the dial 30 also causes folding of the IOL 16. In some additional embodiments, rotation of the dial may result in straightening, or splaying, of one or more of the haptic extensions 34 of the IOL 16. In certain embodiments, the protrusion 60 may extend orthogonally from a longitudinal axis, L, of the IOL cartridge 12 to lock the dial 30 against the ledge 58.

The plunger case 26 may be a hollow and rigid member extending from the housing 18. A plunger 36 may be movably disposed within the plunger case 26 to deliver the IOL 16. The plunger 36 may be an elongated member configured to deliver the IOL 16. Although only a tail end of the plunger 36 is illustrated, the plunger 36 extends lengthwise within the plunger case 26. The plunger case 26 may include an end 66. The end 66 of the plunger case 26 may include a rotatable locking cap 64 including an aperture 68. Upon rotation of the locking cap 64, the aperture 68 may receive a distal end 70 of the push rod 42 that may be movably disposed within a housing 73 of the handpiece 40. In some examples, the aperture 68 may be shaped such that only upon rotation would the push rod 42 be able to enter the aperture 68. Upon actuation, the push rod 42 drives the plunger 36 forward.

Figure 2A:
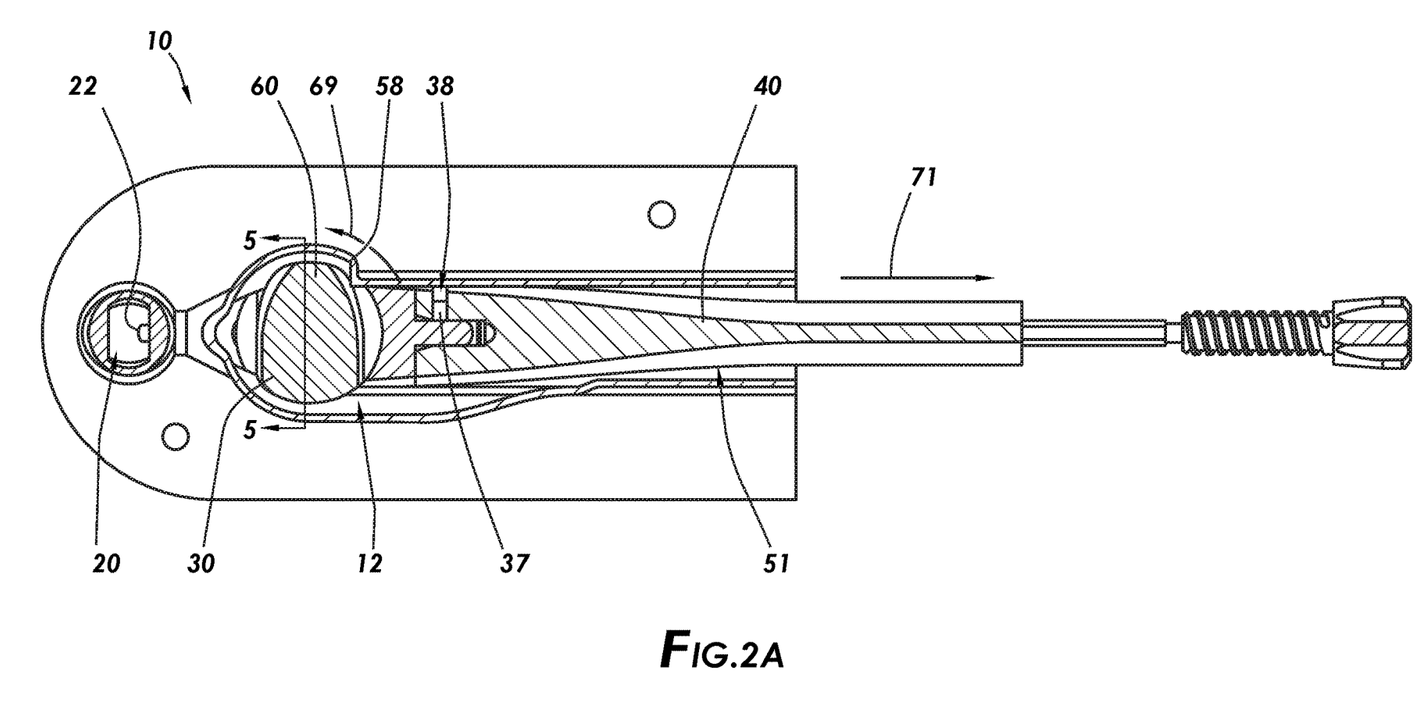
FIG. 2A illustrates a cutaway top view of the packaging with the dial in an initial non-rotated position, in accordance with some embodiments of the present disclosure.

FIG. 2A illustrates a cutaway top view of an insertion tool 51 positioned within the packaging 10 in accordance with some embodiments of the present disclosure. The insertion tool 51 comprises the IOL cartridge 12 that is removably coupled to the handpiece 40. As shown, the projection 37 of the IOL cartridge 12 has been mated with the slot 38 of the handpiece 40. In the illustrated embodiment, the nozzle 22 is in an initial position within the cavity 20 of the packaging 10. As illustrated, the dial 30 is in an initial non-rotated position. The protrusion 60 of the dial 30 extends into and abuts the ledge 58 of the passage 14 of the packaging 10. Rotational movement of the dial 30 upon withdrawal from the passage 14 is indicated by directional arrow 69. A withdrawal direction of the insertion tool 51 from the packaging 10 is indicated by directional arrow 71.

Figure 2B:
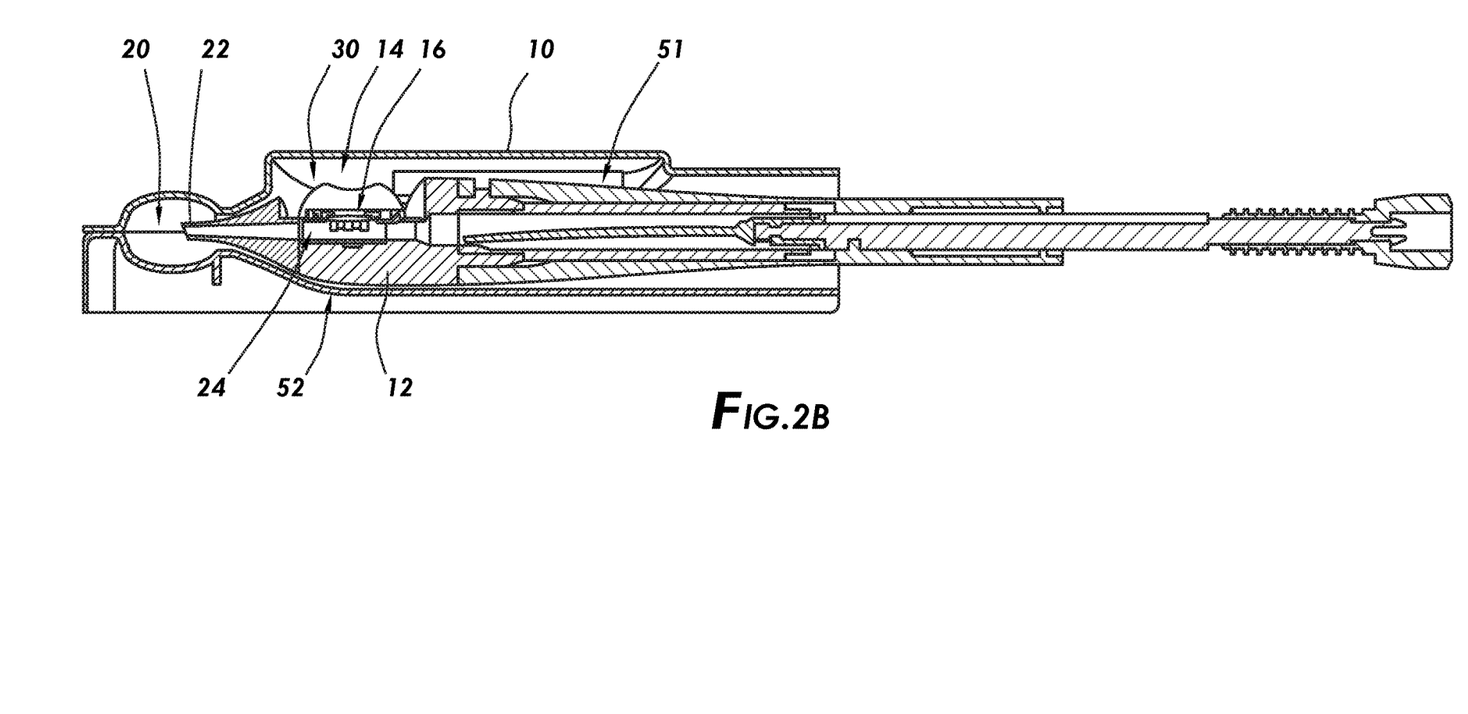
FIG. 2B illustrates a side cross-sectional view of the packaging containing the IOL cartridge, in accordance with some embodiments of the present disclosure.

FIG. 2B illustrates a cross-sectional side view of the insertion tool 51 disposed within the packaging 10, in accordance with some embodiments of the present disclosure. As illustrated, the dial 30 is disposed directly above the compartment 24 containing the IOL 16, such that the dial 30 forms a boundary of the compartment 24, in some examples. The nozzle 22 may be disposed within the cavity 20. In some examples, the passage 14 may include an interior surface 52 that may match contours of the insertion tool 51, to allow a snug fit of the insertion tool 51 within the packaging 10. The interior surface 52 may also be smooth to facilitate sliding of the insertion tool 51 during removal from the packaging 10.

Figure 3:
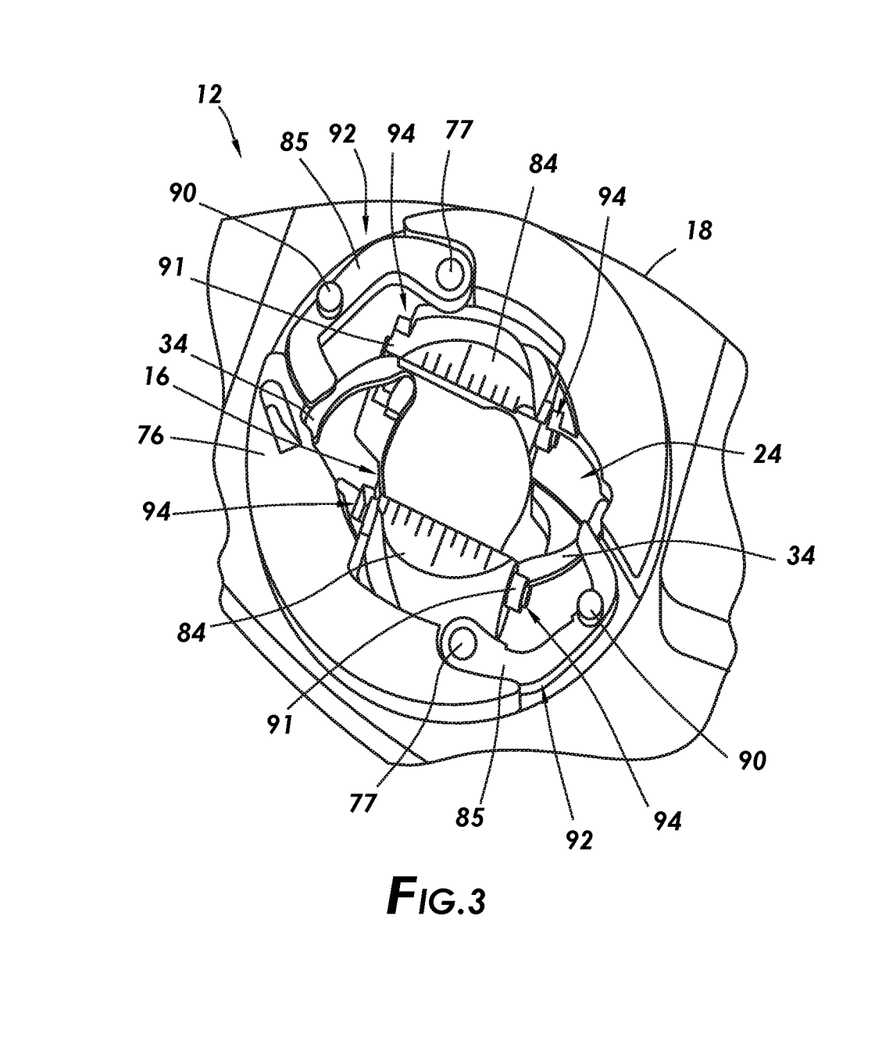
FIG. 3 illustrates a cut away view of components beneath the dial of the IOL cartridge, in accordance with some embodiments of the present disclosure.

FIG. 3 illustrates a cutaway top view of the compartment 24 of the IOL cartridge 12 in accordance with some embodiments of the present disclosure. The dial 30 (e.g., shown on FIG. 1) is not shown in order to illustrate an unobstructed top view of components positioned directly below the dial 30. The compartment 24 may contain edge rollers 84 that are pivotably disposed within the compartment 24. The edge rollers 84 may be used to fold the IOL 16. As illustrated, the IOL 16 may be disposed between the edge rollers 84. The edge rollers 84 may include top pins 91 extending laterally from upper portions of the edge rollers 84. The top pins 91 are positioned to contact an inner surface (not shown) of the dial 30 (e.g., shown on FIG. 1), upon rotation of the dial 30. Rotation of the dial 30 causes the edge rollers 84 to rotate upward and inward, thereby folding the IOL 16. The compartment 24 may also include recesses 94 that are pivot points for the edge rollers 84. The dial 30 may be disposed directly above the compartment 24 and may be supported by an internal portion 76 of the housing 18 of the IOL cartridge 12. The internal portion 76 encompasses, surrounds, or generally defines boundaries for the compartment 24, in some examples.

Compression arms 92 may be pivotably coupled to the internal portion 76 of the housing 18 via connecting pins 77 and may extend into the compartment 24. The compression arms 92 may include protrusions 90 extending from an upper surface 85 of the compression arms 92 to contact an inner surface (not shown) of the dial 30 (e.g., shown on FIG. 1) upon rotation of the dial 30. Rotation of the dial 30 causes the compression arms 92 to move inward thereby folding or compressing the haptic extensions 34 of the IOL 16. The inward movement of the compression arms 92 may be simultaneous with the inward and upward movement of the edge rollers 84 to fold and compress the IOL 16 for delivery into an eye.

Figure 4:
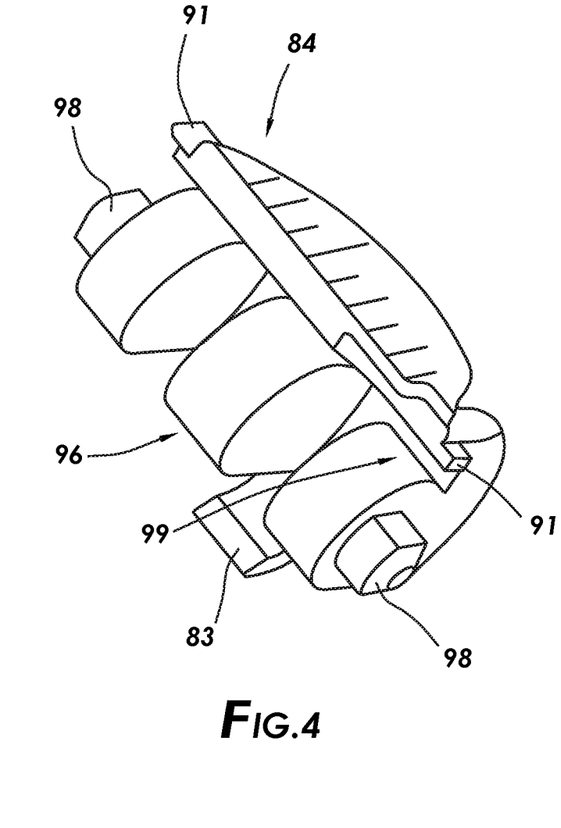
FIG. 4 illustrates a side perspective view of an edge roller of the IOL cartridge, in accordance with some embodiments of the present disclosure.

FIG. 4 illustrates a side perspective view of an edge roller 84 in accordance with some embodiments of the present disclosure. The edge roller 84 may include a cam 96 extending along a length of the edge roller 84. The cam 96 may include cam pins 98 that allow the edge roller 84 to rotate within the recesses 94 (e.g., shown on FIG. 3). The top pins 91 may be moved inward by the dial 30 (shown on FIG. 1). The edge roller 84 may also include a recess 99 to receive the IOL 16 (e.g., shown on FIG. 3). For example, a portion of the IOL 16 (shown on FIG. 3) may be disposed in the recess 99 of each edge roller 84. The recess 99 may extend along a length of the edge roller 84. As the edge roller 84 rotates upward and inward, via the cam pins 98, the IOL 16 folds. Additionally, the edge roller 84 may include a tail portion 83 that may prevent backward rotation of the edge roller 84 as the edge roller 84 is rotated upward and inward, upon rotation of the dial 30 (e.g., shown on FIG. 1).

Figure 5:
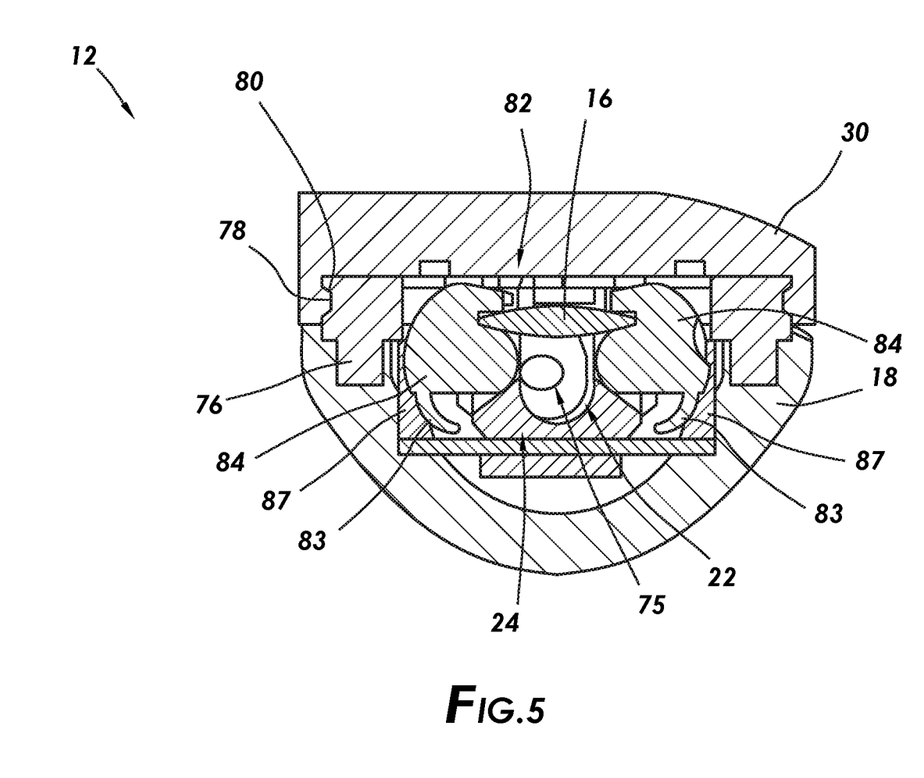
FIG. 5 illustrates a cross-sectional view of the IOL cartridge with the dial in a non-rotated position, in accordance with some embodiments of the present disclosure.

FIG. 5 illustrates a cross-sectional view of the IOL cartridge 12 of FIG. 2A, in accordance with some embodiments of the present disclosure. The dial 30 may be disposed directly above the compartment 24 and may be supported by the internal portion 76 of the housing 18 of the IOL cartridge 12. The dial 30 may rotate about the internal portion 76 and may include a lip 78 that corresponds with a groove 80 of the internal portion 76 to secure the dial 30 to the internal portion 76 of the housing 18. An inner surface 82 of the dial 30 may be exposed to the compartment 24. The inner surface 82 may be contoured to contact or mate with the top pins 91 (e.g., shown on FIG. 3) of the edge rollers 84, upon rotation of the dial 30. The edge rollers 84 may rotate upward and inward, upon rotation of the dial 30, thereby folding the IOL 16. The inner surface 82 may also be contoured to contact or mate with the protrusions 90 (e.g., shown on FIG. 3) of the compression arms 92 (e.g., shown on FIG. 3), upon rotation of the dial 30. Rotation of the dial 30 moves the compression arms 92 inward to compress the haptic extensions 34 (e.g., shown on FIG. 3) of the IOL 16. The tail portions 83 contact and ride upward along tapered walls 87 of the compartment 24. The tail portions 83 may prevent backward rotation, via interaction with one or more features of the tapered walls 87, of the edge rollers 84 as the edge rollers 84 are rotated upward, upon rotation of the dial 30. A passage 75 may extend from the compartment 24 and through the nozzle 22 to receive the IOL 16 in a folded state.

Figure 6:
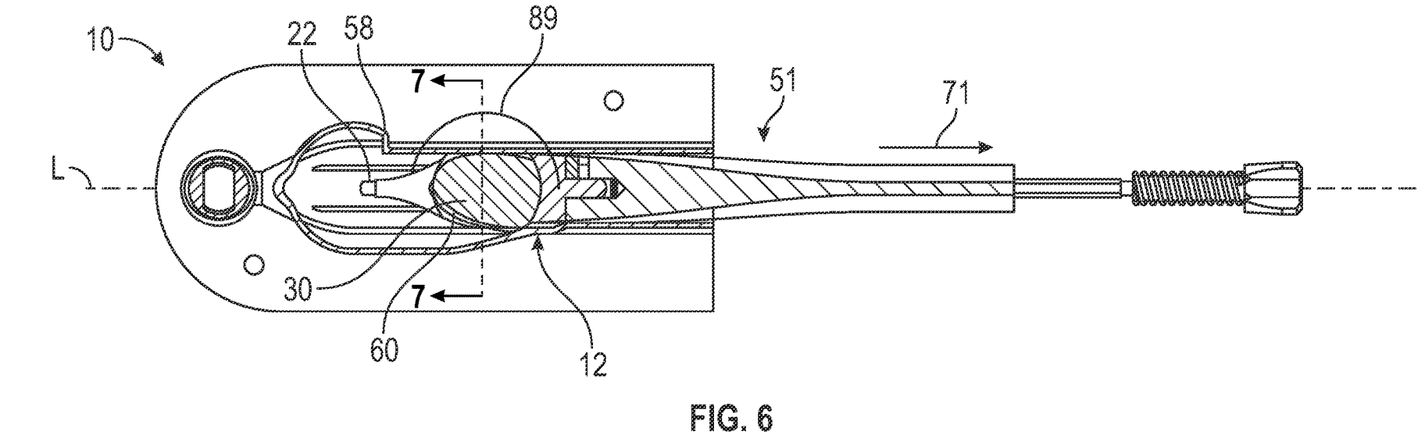
FIG. 6 illustrates a cutaway top view of the IOL cartridge being extracted from the packaging, in accordance with some embodiments of the present disclosure.

FIG. 6 illustrates a cutaway top view of the insertion tool 51 being pulled from the packaging 10 in accordance with some embodiments of the present disclosure. As shown, the dial 30 has been rotated (e.g., 90°) to release the insertion tool 51 from its locked position against the ledge 58 within the packaging 10. The rotation of the dial 30 is indicated by a directional arrow 89, and a pulling direction is indicated by a directional arrow 71. As illustrated, the dial 30 has rotated such that the protrusion 60 of the dial 30 has rotated away from the ledge 58 and toward the longitudinal axis, L, thereby releasing the IOL cartridge 12 and thus the insertion tool 51 from its initial locked position within the passage 14. Additionally, rotation of the dial 30 folds, or otherwise manipulates, the IOL 16 (e.g., shown on FIG. 3) for delivery through the nozzle 22.

Figure 7:
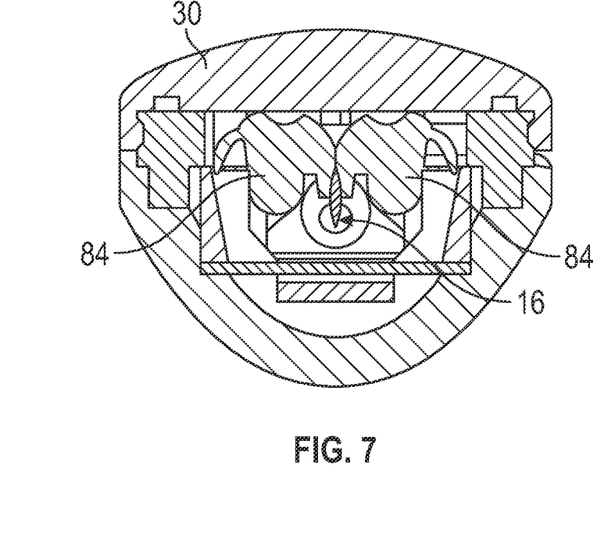
FIG. 7 illustrates a cross-sectional view of the IOL cartridge with the dial in a rotated position, in accordance with some embodiments of the present disclosure.

FIG. 7 illustrates a cross-sectional view of a portion of the IOL cartridge 12 of FIG. 6, in accordance with some embodiments of the present disclosure. As shown, the dial 30 has rotated such that the edge rollers 84 have rotated to fold the IOL 16. Also, the compression arms 92 (e.g., shown on FIG. 3) have rotated inward to compress the haptic extensions 34 (shown on FIG. 3) of the IOL 16.

Figure 8:
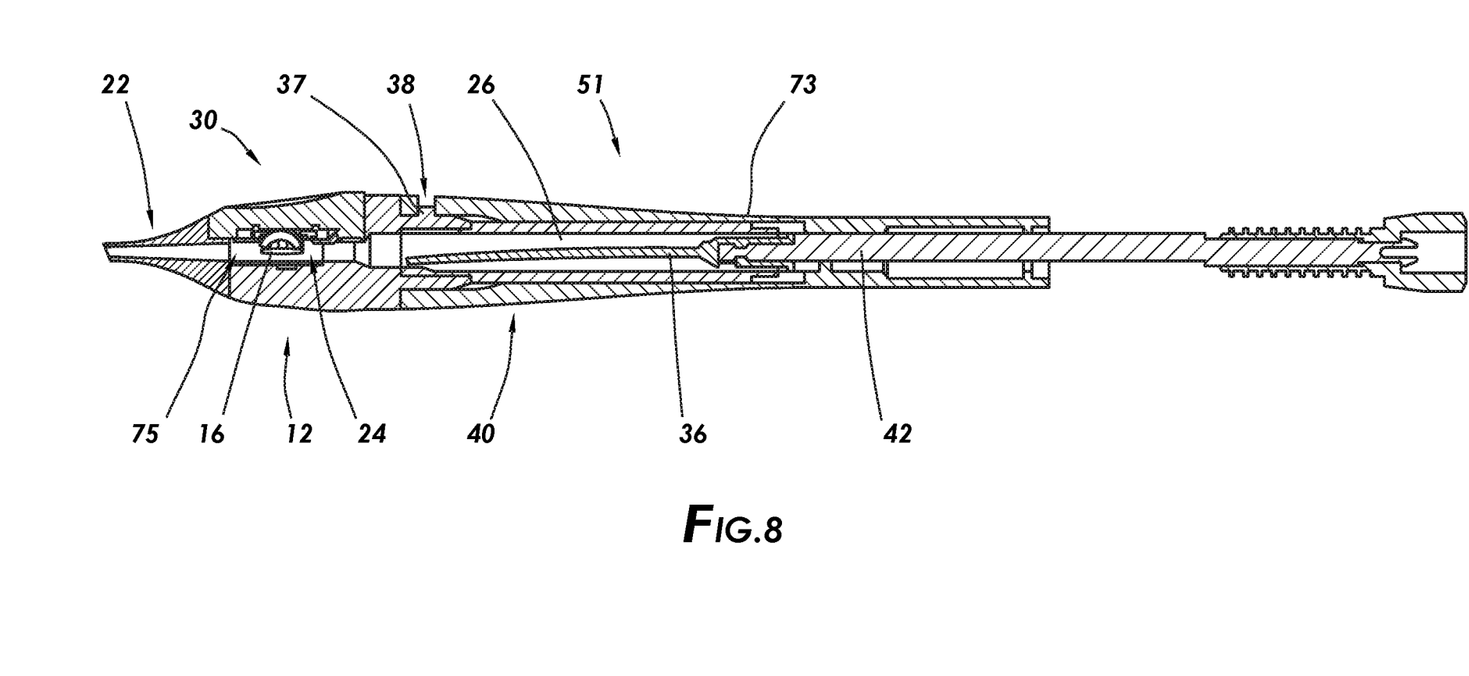
FIG. 8 illustrates the IOL cartridge removably attached to a handpiece, in accordance with some embodiments of the present disclosure.

FIG. 8 illustrates a side view cross-section of the insertion tool 51 that includes the IOL cartridge 12 removably attached to the handpiece 40 in accordance with particular embodiments of the present disclosure. The plunger case 26 may be inserted into the housing 73 of the handpiece 40. The projection 37 of the IOL cartridge 12 may be received and locked into the slot 38 of the handpiece 40 thereby securing the IOL cartridge 12 to the handpiece 40. The plunger case 26 may be in fluid communication with the compartment 24. As previously noted, the plunger 36 may be movably disposed within the plunger case 26. The push rod 42 of the handpiece 40 may be actuated to advance the plunger 36 forward to deliver the IOL 16, in a folded state, from the compartment 24 through the passage 75 and the nozzle 22, and into a patient's eye. After delivery of the IOL 16, the nozzle 22 may be removed from the patient's eye, and the handpiece 40 may be rotated in an opposite direction to disengage the IOL cartridge 12 from the handpiece 40. The used IOL cartridge 12 may then be disposed.

With reference to FIGS. 1-8, an exemplary technique for assembling the IOL cartridge 12 (e.g., shown on FIG. 1) to a handpiece (e.g., the handpiece 40 shown on FIG. 1) to form the insertion tool 51 (e.g., shown on FIG. 8) in accordance with particular embodiments of the present disclosure is described as follows.

First, the packaging 10 may be provided (e.g., shown on FIG. 2A). The IOL cartridge 12 (e.g., shown on FIG. 2A) may be removably disposed within the packaging 22. The dial 30 of the IOL cartridge 12 may be in an initial non-rotated position with a portion (e.g., a protrusion 60 shown on FIG. 1 and FIG. 2A) of the dial 30 adjacent to and/or in contact with the ledge 58 of the internal passage 14 of the packaging 10. Second, the handpiece 40 may be inserted into the passage 14 of the packaging 10 (e.g., see FIG. 2A) and rotated such that a portion of the IOL cartridge 12 (e.g., the projection 37 shown on FIG. 2A) may be received into the slot 38 of the handpiece 40 (e.g., shown on FIG. 2A) thereby securing the IOL cartridge 12 to the handpiece 40 to form the insertion tool 51. Then, the insertion tool 51 may be removed from the packaging 10 by pulling the handpiece 40 out from the packaging 10 (e.g., see FIG. 6). Pulling the insertion tool 51 causes rotation of the dial 30 of the IOL cartridge 12 to release the IOL cartridge 12 from the passage 14 of the packaging 10 (e.g., see FIG. 6) while simultaneously folding the IOL 16 (e.g., see FIG. 7). As previously mentioned, in additional or alternative embodiments, rotation of the dial 30 may additionally or alternatively cause one or more portions, such as haptic extensions 34, of the IOL 16 to be straightened or splayed. Upon actuation of the push rod 42 (e.g., shown on FIG. 8), the plunger 36 advances forward to deliver the IOL 16 from the compartment 24 of the IOL cartridge 12 through the nozzle 22 into a patient's eye. To disassemble the insertion tool 51 (e.g., shown on FIG. 8) after delivery of the IOL 16, the handpiece 40 may be rotated in an opposite direction, thus disengaging the projection 37 of the IOL cartridge 12 from the slot 38 of the handpiece 40. Next, the IOL cartridge 12 may be pulled out from the handpiece 40.

Figure 9A:
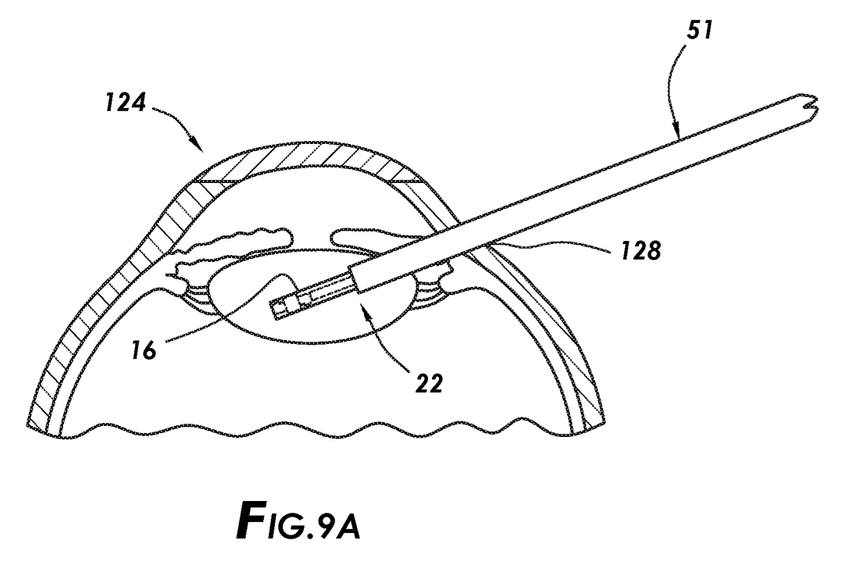
FIGS. 9A and 9B illustrate implantation of the IOL in accordance with some embodiments of the present disclosure.
Figure 9B:
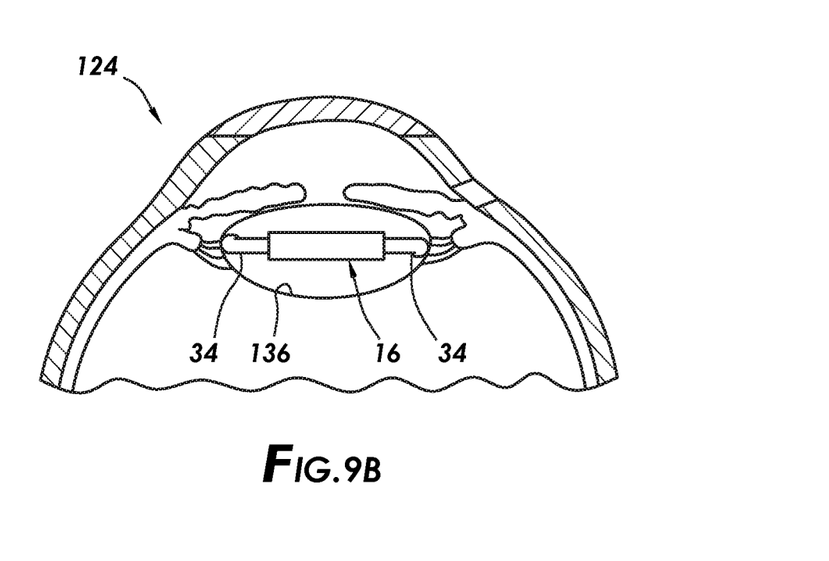

FIGS. 9A and 9B illustrate an exemplary technique for implantation of the IOL 16 into an eye 124 of a patient in accordance with particular embodiments of the present disclosure. FIG. 9A illustrates an incision 128 that may be made in the eye 124 by a surgeon. For example, the incision 128 may be made through the sclera of the eye 124. The incision 128 may be a suitable width or length. Without limitation, the suitable width and/or length may be less than 3 millimeters, and in some instances may be less than 2 millimeters. After the incision 128 is made, the nozzle 22 of the insertion tool 51 may be inserted through the incision 128 into the eye 124. The insertion tool 51 may be actuated to dispense the IOL 16 into a capsular bag 136 of the eye 124, as shown on FIG. 9B.

The IOL 16 may be delivered in a folded (or rolled configuration) and allowed to unfurl after ejection from the insertion tool 51. Upon dispensation, the IOL 16 should unfurl and settle within the capsular bag 136 of the eye 124, as shown on FIG. 9B. The haptic extensions 34 may be manipulated, for example, to engage an equator of the capsular bag 136. The haptic extensions 34 may engage the capsular bag 136 to secure the IOL 16 in the capsular bag 136.

Use of the methods and systems described herein may provide numerous benefits and advantages over other IOL delivery systems. For example, unpackaging of the IOL cartridge and folding or other manipulation of the IOL may be streamlined. Furthermore, the integrated functionality of the packaging causing the rotation of the dial to cause actuation of an IOL folding or straightening mechanism may ensure that the IOL delivery systems are used correctly and may guard against user errors. For example, built-in automated and simultaneous actuation of the dial as the IOL cartridge is removed from the packaging may ensure that the IOL is properly folded or otherwise manipulated prior to ejection of the IOL from the IOL cartridge. Additionally, the positioning of the IOL cartridge within the packaging may ensure that the handpiece, or drive mechanism, be properly attached to the IOL cartridge before the user is able to remove the IOL cartridge from the packaging and actuate the push rod of the handpiece. Altogether, these features and designs may ensure a proper sequence of steps followed by the user to properly operate the IOL delivery systems.

Additionally, the interchangeable utilization between different drive mechanisms and the preloaded IOL cartridge offers a simplified and uniform process for pairing drive mechanisms to preloaded IOL cartridges. Thus, a variety of handpieces employing different types of drive mechanisms may be used with each of numerous different types of IOL cartridges, and therefore different types of IOLs. For example, a user may readily select between multiple types of drive mechanisms he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A system for storing or shipping an intraocular lens (IOL), the system comprising:
   a packaging comprising a passage; and
   an IOL cartridge removably disposed within the passage, the IOL cartridge comprising:
      a compartment configured to receive an IOL; and
      a dial configured to rotate upon withdrawal of the IOL cartridge from the passage, wherein rotation of the dial results in configuration of the IOL for delivery and releases the IOL cartridge from the packaging, wherein:
         the rotation of the dial causes the IOL to be folded,
         the compartment of the IOL cartridge comprises edge rollers configured to rotate and fold the IOL, the IOL disposed between the edge rollers, wherein a surface of each of the edge rollers is configured to contact an inner surface of the dial, wherein the inner surface of the dial is exposed to the compartment, and
         the IOL cartridge further comprises compression arms configured to compress haptic extensions of the IOL, the compression arms configured to contact the inner surface of the dial.

2. The system of claim 1, wherein the passage comprises an internal feature adapted to interact with the dial and cause the dial to be rotated as the IOL cartridge is withdrawn from the packaging.

3. The system of claim 2, wherein:
   the internal feature of the passage comprises a ledge, and
   the dial comprises a protrusion that is adjacent to the ledge, the protrusion configured to be actuated upon contacting the ledge.

4. The system of claim 3, further comprising a plunger case in fluid communication with the compartment, wherein the plunger case comprises a projection configured to attach the plunger case to a handpiece, wherein a plunger is movably disposed within the plunger case.

5. The system of claim 1, wherein:
   the IOL cartridge further comprises a nozzle; and
   the packaging further comprises a cavity in fluid communication with the passage, the cavity configured to house the nozzle of the IOL cartridge.

6. The system of claim 1, wherein the rotation of the dial causes at least one of the haptic extensions of the IOL to be straightened.

7. The system of claim 1, wherein the passage is configured to receive a handpiece for removable attachment of the handpiece to the IOL cartridge.

8. A system for storing or shipping an intraocular lens (IOL) cartridge, comprising:
   a packaging comprising a passage, wherein a ledge is disposed within the passage; and
   an IOL cartridge removably disposed within the passage, the IOL cartridge comprising:
      a compartment for containing an IOL; and
      a dial comprising a protrusion, the dial configured to be rotated from a first position to a second position as a result of interaction between the protrusion of the dial and the ledge of the passage, wherein:
         rotation of the dial from the first position to the second position causes the IOL to be folded,
         the compartment of the IOL cartridge comprises edge rollers configured to rotate and fold the IOL, the IOL disposed between the edge rollers, wherein a surface of each of the edge rollers is configured to contact an inner surface of the dial, wherein the inner surface of the dial is exposed to the compartment, and
         the IOL cartridge further comprises compression arms configured to compress haptic extensions of the IOL, the compression arms configured to contact the inner surface of the dial.

9. The system of claim 8, wherein the protrusion of the dial extends away from a longitudinal axis of the IOL cartridge.

10. The system of claim 9, wherein the protrusion of the dial, in the first position, extends orthogonally relative to the longitudinal axis of the IOL cartridge.

11. The system of claim 10, wherein the protrusion of the dial is configured to rotate inward toward the longitudinal axis of the IOL cartridge upon withdrawal of the IOL cartridge from the packaging.

12. The system of claim 11, wherein the protrusion of the dial is configured to rotate inward and away from the ledge of the passage.

13. The system of claim 8, wherein the protrusion of the dial, in the first position, is configured to lock the IOL cartridge against the ledge of the passage until the rotation of the dial.

14. A method for delivery of an intraocular lens (IOL) into an eye, comprising:
   inserting a handpiece into packaging comprising an IOL cartridge, the IOL cartridge comprising:
      a compartment comprising the IOL;
      a dial, wherein an inner surface of the dial is exposed to the compartment;
      a plunger case in fluid communication with the compartment, wherein a plunger is movably disposed within the plunger case;
   rotating the handpiece to removably attach the handpiece to the IOL cartridge to form an insertion tool; and
   withdrawing the insertion tool from the packaging thereby causing actuation of the dial to configure the IOL for delivery and to release the IOL cartridge from the packaging.

15. The method of claim 14, wherein the actuation of the dial causes the dial to rotate from a first, locked position to a second, unlocked position.

16. The method of claim 15, wherein:
   the dial comprises a first feature; and
   the packaging comprises a second feature configured to engage the first feature of the dial to cause the dial to rotate from the first, locked position to the second, unlocked position as the insertion tool is withdrawn from the packaging.

* * * * *